United States Patent [19]

Cragoe, Jr. et al.

[11] Patent Number: 4,537,902

[45] Date of Patent: Aug. 27, 1985

[54] 4-SUBSTITUTED-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.; Haydn W. R. Williams, Dollard des Ormeaux, Canada

[73] Assignees: Merck & Co., Inc.; Merck Sharp & Dohme (I.A.) Corp., both of Rahway, N.J.

[21] Appl. No.: 47,412

[22] Filed: Jun. 11, 1979

[51] Int. Cl.³ .................. C07D 403/02; C07D 207/40; A61K 31/40

[52] U.S. Cl. .................................. 514/422; 514/425; 548/465; 548/548

[58] Field of Search .............. 260/326.5 C, 326.5 FM, 260/326.13 D; 548/548, 465

[56] References Cited

U.S. PATENT DOCUMENTS 3,340,263  9/1967  Staehelin et al. ......... 260/326.5 FM

*Primary Examiner*—Glennon H. Hollrah
*Assistant Examiner*—D. B. Springer
*Attorney, Agent, or Firm*—Michael C. Sudol, Jr.; Raymond M. Speer; Daniel T. Szura

[57] ABSTRACT

Novel 4-substituted-3-hydroxy-3-pyrroline-2,5-diones are disclosed which inhibit glycolic acid oxidase and thus are useful in the treatment and prevention of calcium oxalate renal lithiasis.

4 Claims, No Drawings

4-SUBSTITUTED-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug therapy specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

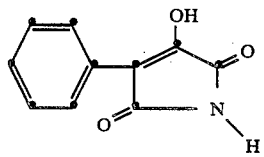

has been described by Harlay, *J. Pharm. Chim.*, 24, 537–48 (1936). 3-Hydroxy-4-aryl-3-pyrroline-2,5-diones are described in U.S. Pat. No. 3,340,263 as intermediates in the preparation of antiphlogistic substances.

A number of 3-hydroxy-4-substitutedphenyl-3-pyrroline-2,5-diones are reported by G. S. Skinner et al., *J. Am. Chem. Soc.*, 73, 2230 (1951). (in this paper these compounds are referred to as pyrrolidine-2,3,5-trione derivatives). 3-Hydroxy-4-(4-bromo-1-naphthyl)-3-pyrroline-2,5-dione is described by G. S. Skinner, *J. Am. Chem. Soc.*, 70, 4011 (1948).

SUMMARY OF THE INVENTION

It has now been found that novel compounds of the formula:

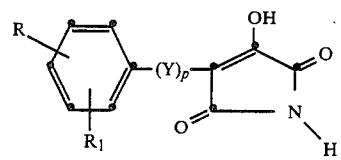

wherein
Y is $(CH_2)_n$; $(CH_2)_m$—O; $(CH_2)_m$—S;
n is 0 to 3;
m is 0 to 2;
p is 0 to 1;
R and $R_1$ are hydrogen, alkyl containing 6 to 12 carbon atoms, cycloalkyl containing 5 to 7 carbon atoms, adamantyl, halogen, with the provisos that if p is 0:
 (a) R and $R_1$ are not both hydrogen;
 (b) R and $R_1$ are not hydrogen and halogen; and
 (c) the R and $R_1$ substitutents are not in ortho positions on the benzene ring,

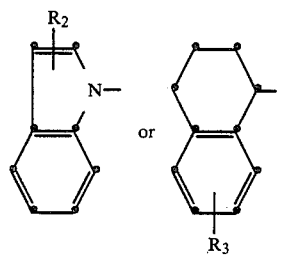

wherein
$R_2$ is loweralkyl or phenyl;
$R_3$ is hydrogen or halogen; or a pharmaceutically acceptable salt thereof, are potent inhibitors of glycolate oxidase. They are, therefore, useful in the treatment and prevention of calcium oxalate kidney and bladder stone disease.

Preferred compounds are those having the structure:

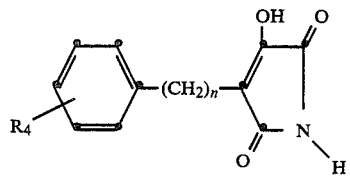

wherein
n is 0 to 3; and
$R_4$ is alkyl containing 6 to 12 carbon atoms, cycloalkyl from 5 to 7 carbon atoms, 1,2,3,4-tetrahydro-1-naphthyl and 4-(2-phenyl-1-indolyl) or a pharmaceutically acceptable salt thereof.

The following compounds known in the prior art have also been found to be useful in inhibiting glycolate oxidase:

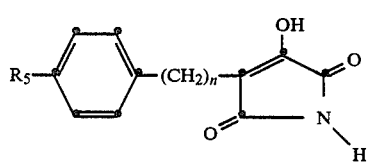

wherein n is 0,

R5 is hydrogen, nitro, methyl or bromo.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

HOCH$_2$C(=O)(O$^-$) —G.O. enzyme→ HC(=O)—C(=O)(O$^-$) —G.O. enzyme→ glycolate    glyoxylate $^-$O—C(=O)—C(=O)—O$^-$

↓ Ca$^{++}$ calcium oxalate

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the kidney and urine. Further, they are useful in the treatment and prevention of renal disease due to calcium oxalate stone formation in the kidney and bladder. They also may be useful in the treatment of the genetically inherited diseases termed Hyperoxaluria types I and II in which very high levels of metabolic oxalate are present.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following general routes:

General Routes

Route 1
R—H
(V)

Step 1 | CH$_3$—C(=O)—Cl
Lewis acid catalyst or acetic anhydride
↓

R—C(=O)—CH$_3$
(III)

Step 2 | Tl(NO$_3$)$_3$
HClO$_4$
CH$_3$OH
↓

R—CH$_2$C(=O)OCH$_3$
(IV)

Step 3 ↘ NH$_3$/CH$_3$OH

Route 2
R—H
(V)

Step 1 | Br—CH$_2$—C(=O)OC$_2$H$_5$
base
↓

R—CH$_2$—C(=O)OC$_2$H$_5$

Step 2 ↙ NH$_3$/CH$_3$OH

R—CH$_2$—C(=O)NH$_2$
(VII)

Step 4 | C$_2$H$_5$O—C(=O)—C(=O)—OC$_2$H$_5$
KOt—Bu
DMF
↓

[pyrrolone ring: R substituent, OH group, two C=O, N—H]

-continued
General Routes

Route 3

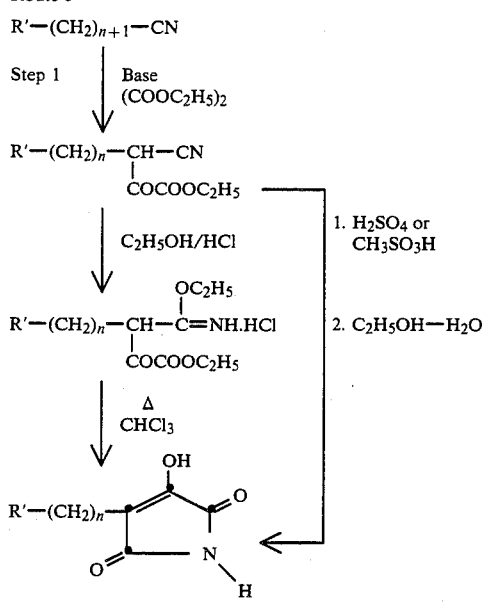

wherein R and R'—(CH₂)ₙ— represent substituents at the 4-position of the 3-hydroxy-3-pyrroline-2,5-dione in formula (I) above.

Route 1 is applicable when p in formula (I) above is 0. Route 2 is applicable when Y in formula (I) above is (CH₂)ₘ—O or (CH₂)ₘ—S. Route 3 is the most generally applicable and is the preferred route in the case when Y in formula (I) above is (CH₂)ₙ and n is 1 to 3. It is also applicable where n is 0.

General Procedure for the Preparation of Phenyl-Substituted Acetophenones

Route 1, Step 1

The methyl ketones (III) are prepared by acetylation of the parent compound (V) with acetyl chloride or acetic anhydride and a Lewis acid catalyst under conventional Friedel Craft conditions.

Examples of methyl ketones (III) prepared by this process are set forth in Table 1 below:

This procedure is suitable where 2 and 3 alkyl and aryl-substituted indoles are used as starting materials.

Preparation of 4-(2-Phenyl-1-indolyl)acetophenone

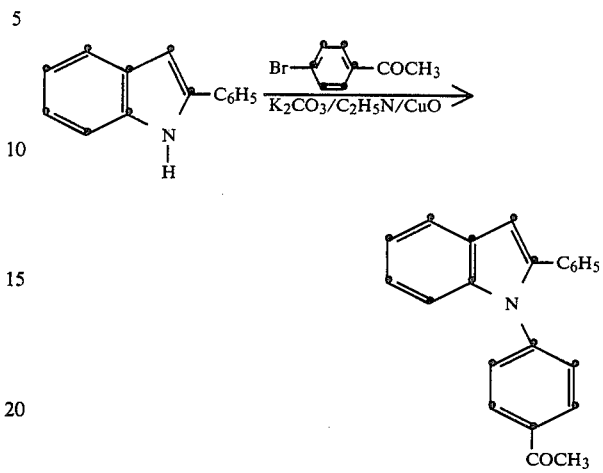

A mixture of p-bromoacetophenone (19.9 g, 0.1 mole), 2-phenylindole (20.26 g, 0.109 mole), cuprous oxide (0.5 g), potassium carbonate (13.82 g) and pyridine (20 ml) was heated in a sealed ampoule at 175° C. for 24 hours in a rocking oven. The cool reaction mixture was poured into water (1 l) and the product was extracted with chloroform (800 ml). The extract was washed with 1N hydrochloric acid (80 ml), then with water (250 ml), then with 1N sodium hydroxide (80 ml) and finally with water (250 ml). The chloroform solution was dried (MgSO₄) and evaporated. Recrystallization of the residue from acetonitrile gave 40.3 g of 4-(2-phenyl-1-indolyl)acetophenone, mp 147°–150° C.

The pure solid crystallized in large prisms, mp 153°–155° C. (from acetonitrile).

Anal. calc'd. for: $C_{22}H_{17}NO$ Calc'd.: C, 84.86; H, 5.50; N, 4.49; Found: C, 84.71; H, 5.69; N, 4.41.

General Procedure for the Preparation of Methyl Substituted Arylacetates (IV)

Route 1, Step 2

Substituted arylacetic acid esters (IV), were made by the oxidative rearrangement of the corresponding

TABLE I

| Compound (III) | Catalyst Solvent | Yield % | MP °C. Solvent | Formula | Analysis Required | Found |
|---|---|---|---|---|---|---|
| 4-cyclohexylacetophenone | AlCl₃ CH₂Cl₂ | 61 | 65–67 petroleum ether | $C_{14}H_{18}O$ | C 3.12 H 8.97 | 83.4 9.07 |
| 4-(1-adamantyl)acetophenone | AlCl₃ CHCl₃ | 65 | | | | |

The methyl ketone, 4-(2-phenyl-1-indolyl)acetophenone, was prepared by the following alternate route.

methyl ketones (III) by the method of E. C. Taylor and A. McKillop, *J. Amer. Chem. Soc.*, 93, 4919 (1971), ibid 95, 3340 (1973). Examples of substituted arylacetic acid esters (IV) prepared by this process are set forth in Table II below.

TABLE II

| Compound (IV) | Yield % | MP °C. Solvent | Formula | Analysis | Required | Found |
|---|---|---|---|---|---|---|
| methyl 4-cyclohexyl-phenylacetate | 98 (crude) | oil | $C_{15}H_{20}O_2$ | | | |
| methyl 4-(1-adamantyl)-phenylacetate | 88 (crude) | 62–65 | $C_{19}H_{24}O_2$ | C<br>H | 80.24<br>8.50 | 79.93<br>8.26 |
| methyl 4-(2-phenyl-1-indolyl)phenylacetate | 56 | 77–79<br>pet. ether | $C_{23}H_{19}NO_2$ | C<br>H<br>N | 80.91<br>5.60<br>4.10 | 80.46<br>5.61<br>3.87 |
| methyl 4-(1,2,3,4-tetra-hydro-1-naphthyl)phenyl-acetate | 89 (crude) | oil | $C_{19}H_{20}O_2$ | | | |

Methyl 4-iodophenylacetate was made by esterifying the commercially available acid.

General Procedure for Preparing the Substituted Acetamides

Route 1, Step 3

The substituted acetic acid esters (IV) were converted to the corresponding amides (VII) by treatment with 7½ parts volume by weight of a saturated solution of ammonia in methanol at room temperature. Conversion to the amide was followed by thin layer chromatography. Examples of substituted acetamides (VII) prepared by this process are set forth in Table III below.

TABLE III

| Compound (VII) | Yield % | MP °C. Solvent | Formula | Analysis | Required | Found |
|---|---|---|---|---|---|---|
| 4-cyclohexylphenylacetamide | 50 | 164–166<br>MeOH | $C_{14}H_{19}NO$ | C<br>H<br>N | 77.38<br>8.81<br>6.45 | 77.86<br>8.66<br>6.61 |
| 4-(1-adamantyl)phenylacetamide | 46 | 154–156<br>MeCN | $C_{18}H_{23}NO$ | C<br>H<br>N | 80.25<br>8.60<br>5.19 | 80.08<br>8.66<br>5.23 |

TABLE III-continued

| Compound (VII) | Yield % | MP °C. Solvent | Formula | Analysis Required | Found |
|---|---|---|---|---|---|
| 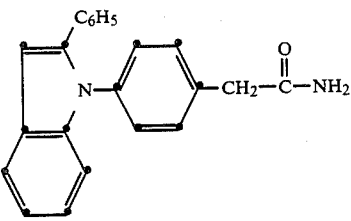 4-(2-phenyl-1-indolyl)phenylacetamide | 95 | 195–196 MeCN | $C_{22}H_{18}N_2O$ | C 80.95<br>H 5.55<br>N 8.58 | 80.77<br>5.61<br>9.00 |
| 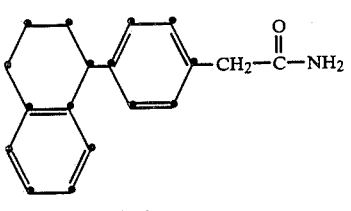 4-(1,2,3,4-tetrahydro-1-naphthyl)phenylacetamide | 27 | 124–126 toluene petroleum ether | $C_{18}H_{19}NO$ | C 81.47<br>H 7.22<br>N 5.28 | 81.29<br>7.16<br>5.07 |
| 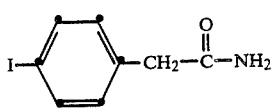 4-iodophenylacetamide | 86 overall | 207.5–208.5 EtOH | $C_8H_8INO$ | C 36.81<br>H 3.09<br>N 5.37 | 36.69<br>3.04<br>5.41 |

Route 2 of the General Routes is applicable when Y is $(CH_2)_m$—O or $(CH_2)_m$—S in formula (I) above.

General Procedure for the Preparation of Esters of Substituted Phenyl-thioacetic and -oxyacetic Acids (VI)

Route 2, Step 1

The corresponding substituted phenol or thiophenol (10 mmole) is added to a solution of sodium (10 mmole) in ethanol (20 ml) under nitrogen. To the cooled mixture is added ethyl bromoacetate (10 mmole) in ethanol (10 ml), and then the mixture is stirred for an appropriate time at room temperature in order to complete the reaction. The ester (VI) is isolated by addition of water and extraction with methylene chloride. The crude ester is used for the preparation of the corresponding amide (VII) without further purification.

In the case wherein m is 1 or 2 in formula (I) above, NaH in DMF or THF in place of sodium and ethanol is used to form the anion before adding ethyl bromoacetate.

General Method for the Preparation of 3-Hydroxy-4-substituted-3-pyrroline-2,5-diones Routes 1 and 2, Step 4

A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolved, the aqueous mixture is extracted with ethyl acetate (2×35 ml) and then acidified with 6N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

Compounds of this type are often solvated after recrystallization (with either DMF, dioxane, isopropanol or acetonitrile) and may require drying at 110° C./0.05 Torr in order to remove the solvate.

TABLE IV

| Compound (I) | Yield % | MP °C. Solvent | Formula | Analysis | Required | Found |
|---|---|---|---|---|---|---|
| 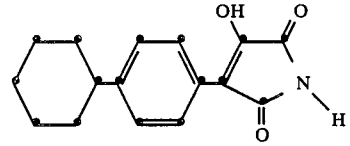<br>3-hydroxy-4-(4-cyclo-hexylphenyl)-3-pyrroline-2,5-dione | 63 | 275–278<br>MeCN | $C_{16}H_{17}NO_3$ | C<br>H<br>N | 70.83<br>6.32<br>5.16 | 70.82<br>6.53<br>5.29 |
| 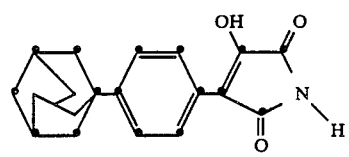<br>3-hydroxy-4-[4-(1-adamantyl)phenyl]-3-pyrroline-2,5-dione | 63 | 313–316<br>MeCN | $C_{20}H_{21}NO_3$ | C<br>H<br>N | 74.28<br>6.54<br>4.33 | 74.29<br>6.63<br>4.50 |
| 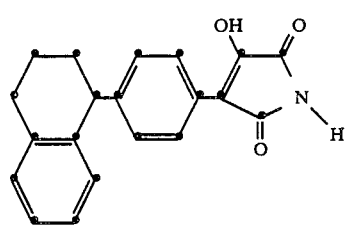<br>3-hydroxy-4-[4-(1,2,3,4-tetrahydro-1-naphthyl)-phenyl]-3-pyrroline-2,5-dione | 36 | 177–179<br>MeOH | $C_{20}H_{17}NO_3$ | C<br>H<br>N | 75.21<br>5.36<br>4.38 | 75.42<br>5.39<br>4.13 |
| 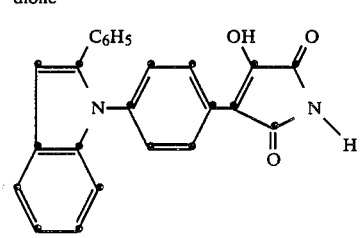<br>3-hydroxy-4-[4-(2-phenyl-1-indolyl)-phenyl]-3-pyrroline-2,5-dione | 37 | 233–235<br>EtOH | $C_{24}H_{16}N_2O_3 \cdot$<br>$C_2H_5OH$ | C<br>H<br>N | 73.22<br>5.19<br>6.56 | 73.46<br>5.48<br>6.74 |

Note:
The compounds of this invention may also be designated 3-substituted-4-hydroxy-3-pyrroline-2,5-dione derivatives.

According to Route 3, the phenylalkylnitrile is reacted with diethyl oxalate in an alcohol such as methanol, ethanol, isopropanol and the like, in the presence of strong base, such as the corresponding sodium or potassium alkoxides. Formation of the anion adjacent to the nitrile group is necessary for reaction to take place. The reaction can be carried out in aprotic solvents such as dimethylformamide or toluene using a strong base, such as sodium and potassium alkoxides, lithium diisopropylamide and the like. The temperature for the reaction can range from 0°–100° C.

The resulting ester nitrile is treated with ethanol saturated with anhydrous hydrogen chloride to give the imino ether. The solvent is evaporated and the residue heated in chloroform to yield the desired 3-hydroxy-3-pyrroline-2,5-dione (see Example 1).

Alternately, the ester nitrile may be dissolved in sulfuric acid or methanesulfonic acid and quenched in ice-water, or ethanol-water, according to the procedures set forth in J. Klosa, Chem. Ber., 85, 229 (1952); U.S. Pat. No. 3,349,263 and Harlay et al., J. Pharm. Chim., 24, 537–48 (1936).

For compounds where $(Y)_p=(CH_2)_n$ and n=1–3, the required nitrile intermediates can be obtained readily starting from the corresponding arylacetic acid ester derivatives by standard chain extension reactions well known in the art. Thus the arylacetic ester intermediate can be reduced with lithium aluminum hydride to the 2-aryl-1-ethanol. Conversion of the ethanol intermediate to the corresponding halide (chloride or bromide) is accomplished with halogenating agents such as phosphorus oxychloride, thionyl chloride, carbon tetrachloride-triphenylphosphine, or phosphorus oxybromide. Reaction of the halide intermediate with cyanide ion provides the next higher homologous nitrile. In some instances it is preferable to convert the ethanol intermediate to the p-toluenesulfonate ester, using p-toluenesulfonyl chloride in pyridine. Displacement of the p-toluenesulfonate group by cyanide ion then provides the homologous nitrile. For further stepwise homologation the nitrile derivative is hydrolysed to the corresponding carboxylic acid, employing aqueous mineral acid or base. The resulting acid, or its methyl or ethyl ester, is reduced to the corresponding alcohol with diborane, or lithium aluminum hydride respectively. The above sequence of halogenation, or p-toluenesulfonate ester formation, followed by displacement of the leaving group with cyanide ion, is then repeated.

Included within the scope of the invention are the pharmaceutically acceptable salts of formula (I) compounds. The compounds of formula (I) are strong organic acids with a pKa in the range 2-4. Thus salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the utilities stated by formulating them in a composition such as tablet, capsule or elixir for oral administration. Sterile solutions or suspensions can be used for parenteral administration. About 10 to 200 mg of a compound of formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose is in the 30 to 2000 mg range and preferably in the 50 to 1000 mg. range.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following example, given by way of illustration and not to be construed as limiting, further clarifies the invention.

EXAMPLE 1

4-Benzyl-3-hydroxy-3-pyrroline-2,5-dione

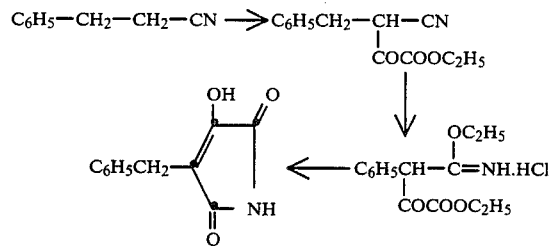

920 mg sodium (40 mmole) is dissolved in 45 ml ethanol and to the ice-bath cooled solution is added 4.66 g diethyl oxalate (31.9 mmole) and 4.17 g hydrocinnamonitrile (31.9 mmole). The mixture is stirred at room temperature for 1 hour, under reflux for 3 hours, and then allowed to stand at room temperature overnight. Evaporation, acidification of the residue, and extraction with methylene chloride affords ethyl 3-cyano-2-oxo-4-phenylbutanoate in 38% yield. The compound crystallizes from petroleum ether in colorless needles; m.p. 80°-83° C.

462 mg ethyl 3-cyano-2-oxo-4-phenylbutanoate is added to ethanol saturated with hydrogen chloride (10 ml) and the mixture is allowed to stand at room temperature overnight. The solvent is evaporated and the residue dried at 0.05 Torr. Dry chloroform is added and the mixture heated under reflux for 3 hours. The chloroform is extracted with excess 2N sodium hydroxide solution, then the aqueous solution is acidified and extracted with chloroform to afford 43 mg (10%) of product; m.p. 140°-142° C.

What is claimed is:

1. 3-Hydroxy-4-(cyclohexyl)phenyl-3-pyrroline-2,5-dione.

2. 3-Hydroxy-4-[4-(2'-phenyl-1-indolyl)phenyl]-3-pyrroline-2,5-dione.

3. A method of treating persons afflicted with calcium oxalate kidney or bladder stones or preventing the formation of calcium oxalate bladder or kidney stones which comprises administering to such a patient an effective amount of a compound having the structure

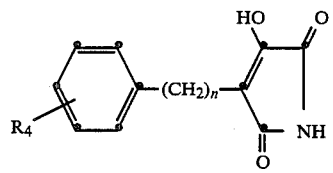

wherein
n is 0 to 3; and
$R_4$ is alkyl having 4 to 12 carbon atoms, cycloalkyl containing from 5 to 7 carbon atoms, iodo 1,2,3,4-tetrhydro-1 naphthyl, 4-(2'-phenyl-1-indolyl)phenyl or a pharmaceutically acceptable salt thereof.

4. A method of treating persons afflicted with calcium oxalate kidney or bladder stones or preventing the formation of calcium oxalate kidney or bladder stones which comprises administering to such a patient an effective amount of a compound having the structure:
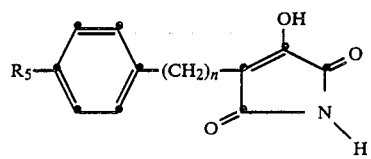
wherein
n is 0;
$R_5$ is hydrogen, nitro, methyl, bromo or iodo.
* * * * *